United States Patent [19]
Loeb et al.

[11] Patent Number: 5,984,915
[45] Date of Patent: Nov. 16, 1999

[54] PERCUTANEOUS LASER TREATMENT

[75] Inventors: Marvin P. Loeb, Huntington Beach; Sanford Damasco, Long Beach, both of Calif.

[73] Assignee: Trimedyne, Inc., Irvine, Calif.

[21] Appl. No.: 08/947,362

[22] Filed: Oct. 8, 1997

[51] Int. Cl.$^6$ .................................................. A61B 17/36
[52] U.S. Cl. ................................................. 606/9; 606/15
[58] Field of Search ........................... 606/3, 9, 13–16; 128/898

[56] References Cited

U.S. PATENT DOCUMENTS

| | | | |
|---|---|---|---|
| 4,862,886 | 9/1989 | Clarke et al. | 606/15 |
| 5,000,752 | 3/1991 | Hoskins et al. | 606/15 |
| 5,201,729 | 1/1993 | Hertzmann et al. | 606/2 |
| 5,312,395 | 5/1994 | Tan et al. | 606/9 |
| 5,360,425 | 11/1994 | Cho | 606/6 |
| 5,370,642 | 12/1994 | Keller | 606/9 |
| 5,380,316 | 1/1995 | Aita et al. | 606/7 |
| 5,389,096 | 2/1995 | Aita et al. | 606/16 |
| 5,531,739 | 7/1996 | Trelles | 606/2.5 |
| 5,569,240 | 10/1996 | Dowlatshahi et al. | 606/15 |
| 5,746,735 | 5/1998 | Furumoto et al. | 606/9 |
| 5,749,868 | 5/1998 | Furumoto | 606/9 |

OTHER PUBLICATIONS

Form No. 002 by the American Society for Dermatologic Surgery, 1996.

Apfelberg et al., Progress Report on Multicenter Study of Laser–Assisted Liposuction, 18 Aesth. Plast. Surg. 259–264 (1994).

Goldman et al., Cutaneous Laser Surgery 200–203 (Mosby 1994).

Ramirez et al., Endoscopic Plastic Surgery 28–35 (Springer 1996).

Bosniak, Ophthalmic Plastic and Reconstructive Surgery 617–625 (W.B. Saunders Company 1996).

Kohn, Textbook of Ophthalmic Plastic and Reconstructive Surgery 178–191 (Lea & Febiger 1988).

*Primary Examiner*—Linda C. M. Dvorak
*Assistant Examiner*—Roy Gibson
*Attorney, Agent, or Firm*—Olson & Hierl, Ltd.

[57] ABSTRACT

A method of percutaneous and subcutaneous laser treatment of the tissue of a patient is provided. The tip of an optical fiber is be passed through the skin, advanced through the tissue subcutaneously to a desired treatment area and withdrawn. Laser energy can be emitted at different levels during any or all of the skin penetration, advancement, tissue treatment and withdrawal phases. The present invention is useful for surgical treatments, and is especially suitable for minimally invasive plastic or cosmetic surgical and dermatological procedures without bleeding and with less edema, erythema and swelling and faster healing than conventional surface laser energy application, abrasion, scalpel surgery or chemical peel procedures.

38 Claims, No Drawings

PERCUTANEOUS LASER TREATMENT

TECHNICAL FIELD

The present invention relates to methods and procedures for the amelioration of cosmetic flaws and the like by the application of laser energy to a selected target region or site. The present invention is useful in the practice of surgery, especially plastic and cosmetic surgery, as well as dermatology. The present invention is especially suitable for minimally invasive surgical treatments in which a percutaneous approach is desired.

BACKGROUND OF THE INVENTION

Biological tissue comprises cells embedded in a primarily proteinaceous extracellular matrix. Collagen is one of the predominant proteins found in the extracellular matrix. Collagen can be altered by the application of thermal energy to become denatured and act as a biological glue. Thermal energy can also cause collagen fibers to become cross-linked, reducing the volume of the thermally treated collagen. The thermal effect may be conveniently produced by the interaction of laser generated light energy with tissue. Laser energy of the appropriate wavelength, energy and geometry can thus be used to weld together opposed tissue surfaces and shrink collagen-containing tissues.

The use of laser devices in various types of surgery is known. Such devices cause thermal coagulation and/or ablation of tissue by emission of a predetermined level of laser energy for a predetermined time. The unwanted tissue can be coagulated to the desired depth by laser energy at low energy density, or ablated by subjecting the tissue to a higher level of energy density. However, when laser energy is applied to the skin from an external source, erythema or sun-burning frequently occurs. The erythema can take weeks or months to subside, and discoloration or scarring of the skin may be a lasting result.

Several plastic surgery procedures involve the surgical removal of subcutaneous fat and excess skin and the tightening of the remaining skin. Such procedures include meloplasty (face lifts), eyebrow lifts and blepharoplasty for removal of bags under the eyes (dermochalasis and blepharochalasis). Beyer, C. K., Baggy lids, *Int. Ophthalmol. Clin.*, 10: 47–53 (1970). Traditional surgical approaches require cutting and removing excess skin and fat using incisions often centimeters in length. These approaches are subject to potential complications such as hemorrhage, hematoma, infection and removal of too much skin or fat (overcorrection). Kohn, R., *Textbook of Ophthalmic Plastic and Reconstructive Surgery*, pp. 177–191, 186, Lea & Febiger, Philadelphia (1988). As an example, surgical procedures for blepharoplasty are complex. Inappropriate or poorly performed surgery may result in an adverse cosmetic result, or may place the patient at risk for developing vision-threatening complications. Custer, P. L., Lower eyelid blepharoplasty, in Bosniak, S., editor, *Principles and Practice of Ophthalmic Plastic and Reconstructive Surgery*, pp. 617–625, 624, W. B. Saunders, Philadelphia (1996).

Lasers have been employed in cosmetic and reconstructive surgery. The Nd:YAG laser has been used to make incisions in the skin for face lifts (meloplasty) and for removal of bags under the eyes by blepharoplasty. Apfelberg, D. B., YAG laser meloplasty and blepharoplasty, *Aesth. Plast. Surg.* 19: 231–235 (1995). However, the Nd:YAG laser's continuous wave energy may be overly thermal and cause an excessively deep zone of penetration (about 4000 $\mu$m). The $CO_2$ laser has been employed in blepharoplasty using the transconjunctival approach. David, L. M. The laser approach to blepharoplasty, *J. Dermatol. Surg. Oncol.* 14: 741–235 (1988). While the use of laser energy has been reported to reduce bleeding during surgery and reduce pain during healing, a large incision is still required. Morrow, D. M., and Morrow, L. B.: $CO_2$ laser blepharoplasty. A comparison with cold-steel surgery, *J. Dermatol. Surg. Oncol.*, 18: 307–313 (1992). The only advantage provided by the described laser technique was less swelling after surgery.

What is needed is a method of plastic surgery using a laser that provides more desirable tissue effects and which can also be used in a minimally invasive percutaneous approach.

SUMMARY OF THE INVENTION

A percutaneous method for the treatment of skin and subcutaneous tissue by means of an appropriate laser device capable of emitting pulses of light energy at an appropriate wavelength of less than 2 micrometers, with relatively short pulse widths, at relatively low energy per pulse and relatively rapid pulse repetition rates is provided by the present invention. Light energy characterized by such parameters is applied subcutaneously to tissues underlying the skin. The method is useful for the practice of surgery, especially plastic and cosmetic surgery as well as dermatology. The method is non-invasive or minimally invasive and well suited for outpatient therapy. In particular, application of the laser energy directly to the tissue beneath the skin eliminates or reduces the erythema that can result when laser energy is applied to the skin from outside the body.

The method of the present invention is especially suitable for several procedures used in plastic and cosmetic surgery as well as dermatology. Procedures for which the method of the present invention can be used include, inter alia, the removal of pigmentation, such as lentigines (age spots), hyperpigmentation, lentigo (freckles), café-au-lait macules, actinic keratosis, melasma, and tattoos (body or facial). The method of the present invention can also be used for the removal of plantar warts, chin reshaping via the percutaneous laser melting or desiccation of fat, amelioration of turkey neck, and the treatment of some dilated blood vessels associated with rosacea. The method of the present invention is also suitable for coagulation of spider veins (<1 mm), removal of keloid scars, coagulation of varicose veins (>1 mm), reshaping of the upper lip, reshaping of the eyelids, permanent ablation of the hair follicle to permanently prevent hair regrowth and some types of otoplasty. The method of the present invention is also suitably used for the treatment of various cutaneous vascular lesions, such as port wine stains, hemangiomas, and telangiectasias, including those of the face and the leg.

The method of the present invention can also be used for plastic surgery treatments such as skin resurfacing, removal of perioral, periorbital and ear lobe wrinkles, treatment of nasal labial folds, perioral fat pads and marionette lines, lip lift, neck lift, eyebrow lift, lipolysis (of upper and lower eyelids, cheeks, abdomen, thighs), blepharoplasty, rhinoplasty, hair transplantation, treatment of polly beak and internal weir (nostril reduction). Scars that can be treated using the method of the present invention include acne scars, keloids, chicken pox scars, stretch marks (striae), hypertrophic scars, and skin graft hypertrophy as well as pits and depressions. In addition, the method of the present invention is also suitable for burn debridement, and for the treatment of corns, papilloma (warts, condylomas, polyps) and skin cancer, including basal cell carcinoma.

A conventional pulsed or continuous wave laser having a wavelength of less than 2 micrometers can be converted, in accordance with the present invention, to produce pulses of variable pulse-width at various energy levels. Suitable lasers include, for example, excimer lasers, argon lasers, KTP lasers, 1.064 μm Nd:YAG lasers, 1.44 μm Nd:YAG lasers, 1.34 μm Nd:YAP lasers, 1.33 μm Nd:SFAP lasers, cobalt-magnesium-fluoride lasers, diode lasers and erbium (1.55 μm erbium:YAG, 1.73 μm erbium:YLF, 1.535 μm Er:Yb fiber and erbium:YSSG) lasers. Different depths of penetration of laser energy in tissue are achievable with these and other lasers. Consequently, different rates of vaporization, different types of tissue effects and different depths of coagulation or collagen shrinkage can be obtained. Alternatively, a source of intense white light such as that obtained from a high intensity white light generator can be used.

Energy from a relatively low power, short pulse-width, high repetition rate laser, applied percutaneously through an optical fiber or hollow waveguide, can avoid burning or charring the skin, or the tissue beneath the skin, while accomplishing the desired beneficial physiologic effect. At lower energy densities, the collagen component of tissue can be cross linked, reducing its volume and causing shrinkage of the tissue. Additionally, the method of the present invention allows for the melting or desiccation of subcutaneous fat by the use of a relatively small diameter optical fiber, e.g. a 25–400 μm core diameter, that is introduced through the skin. The small diameter of the optical fiber, coupled with the low energy used, typically about 3 to 100 milliJoules per pulse (mJ/pulse), the narrow pulse-width, typically less than 200 microseconds (μS), and relatively fast repetition rate, generally 20 to 80 pulses per second (Hz), allow the fiber to penetrate the skin and be used subcutaneously upon tissue without perceptible charring as a result. Preferably, an energy level of about 3 mJ/pulse to about 20 mJ/pulse is used while the tip of the optical fiber is inserted through the skin.

A laser containing two or more laser energy producing cavities (resonators) may employ a mechanism for either producing a rapid train of single, evenly spaced pulses up to 80 Hz, or emitting one pulse alongside another (double pulse) with a pulse width of up to 700 μS at a frequency up to 40 Hz, for greater coagulative effect or for vaporizing relatively harder tissues, such as bone.

The laser source typically comprises a housing containing the laser generating unit as well as optical and electronic control components therefor. The optical fiber is connected proximally to the light output of the laser and extends distally through a hand piece held by the surgeon. The light energy produced by the laser source is introduced into the proximal end portion of the optical fiber, which itself passes through a handpiece, and is emitted from the bare distal tip of the optical fiber distally to the target tissue. The tip of the optical fiber preferably has a core diameter of about 25 μm to 400 μm, more preferably about 50 μm to about 200 μm.

The face of the optical fiber tip is preferably aligned at a right angle to its longitudinal axis. Alternatively, the face of the optical fiber tip can be aligned at an angle of less than 90 degrees to its longitudinal axis, producing a beveled end that facilitates fiber entry through the skin. In other embodiments, the tip of the optical fiber is conical or wedge-shaped. Once inside tissue, endogenous fluids, or injected fluids, such as saline or local anesthetic, cause the fiber to emit laser energy in a manner similar to an optical fiber that has an end face aligned at a right angle to its longitudinal axis.

In order to obviate or at least minimize thermal damage, scarring and pigmentation changes of the skin at the entry point of the optical fiber, the fiber preferably is passed through the skin without lasing through an existing opening in the skin provided by a trocar puncture or through the entry site of a hypodermic needle used to inject saline and/or anesthetic.

Lasing can be commenced after the fiber is at least about 2–3 mm into the tissue. Lasing is stopped on fiber withdrawal when the distal end of the fiber is about 2–3 mm from the entry point.

Alternatively, bleeding at the entry and exit point can be minimized by lasing at extremely low energy, as low as 1 mJ/pulse with a very short pulse width, preferably 10–30 μS, during insertion or withdrawal of the optical fiber through the skin.

In another embodiment, the bare distal tip of the optical fiber is encased or slidably disposed within a hypodermic needle which is inserted through the skin at about a ninety-degree angle (normal to the surface). Once through the skin, the hypodermic needle and optical fiber together are aligned to a course substantially parallel to the skin and to or through underlying tissue. The hypodermic needle and optical fiber together, or the optical fiber alone, are advanced through the tissue.

The method aspect of the present invention includes a subcutaneous advancement phase as well as a withdrawal phase. In use, after penetration of the skin as described above, the tip of the optical fiber is moved forwardly through the tissue during the advancement phase. During this phase, the tip of the optical fiber is advanced through the tissue for the desired distance without emission of laser energy or with laser emission at a controlled power level chosen to achieve the effect desired. If desired, laser energy can be emitted from the tip during advancement at a controlled energy level of less than about 3 to about 20 mJ/pulse, at a frequency of 20 to 80 Hz and a pulse width of 30 to 100 μS. A preferred energy emission frequency during the advancement phase is about 50 to 60 Hz. During advancement, very low emission energy of 3–10 mJ/pulse can be used to facilitate the advancement of the optical fiber and prevent tissue adherence to the optical fiber. If desired, laser energy to obtain a desired therapeutic effect can be emitted at an energy of 5 to 50 mJ/pulse.

The tip of the optical fiber may be maintained at the position of furthest advance and laser energy emitted there, or alternatively, the tip may be immediately withdrawn. During the period while the tip of the laser probe is being used to treat the tissue at a selected site, laser energy can be emitted at an energy of about 5 to about 50 mJ per pulse at a frequency of about 20 to about 60 Hz. During the withdrawal phase, laser energy can be emitted at about 5 to about 50 mJ/pulse at a frequency of about 20 to about 60 Hz, depending on the tissue effect desired, or at about 3 to about 10 mJ/pulse to prevent tissue adhering to the fiber during withdrawal. In other cases, the fiber can be withdrawn without using laser energy. The energy level can also be changed as the fiber moves from one area to another under the skin to obtain a desired effect. It is not necessary to remove the optical fiber, or to turn off the laser while the surgery is being performed, In general, the level of light energy emitted during the withdrawal phase is equal to or greater than the emission level, if any, during the advancement phase. The power output, frequency and pulse-width can be varied as required to achieve the desired result, based on the surgeon's clinical experience.

DETAILED DESCRIPTION OF THE INVENTION

The method of the present invention initially produces a subcutaneous tunnel or cavity through the tissue as the tip of the optical fiber is moved forwardly during the advancement stage, or rearwardly during the withdrawal stage, usually while emitting light energy at a relatively low energy level and a relatively short pulse width. However, in some cases, for example, if extremely thin skin could be damaged by emitting light energy during advancement or withdrawal, the tip of the optical fiber can be advanced or withdrawn without emitting light energy. Likewise, the tip of the optical fiber can be advanced via a hypodermic needle or a cannula through friable tissue without emitting light energy.

The selected area is treated by repeated advancement and withdrawal cycles of the tip of the optical fiber as appropriate. These cycles may be performed in one or more directions through the same opening made by the insertion of the fiber or by the hypodermic needle containing the fiber. Each cycle may be directed at the same or a different radial angle. However, to avoid damage to blood vessels which may be situated substantially normal to the skin's surface, the optical fiber is moved unidirectionally rather than so as to sweep laterally through a sector like a windshield wiper. Advancement and withdrawal cycles are repeated as appropriate through other openings within the selected region, until the entire region has been treated. The position of the tip of the optical fiber during treatment is controlled in three dimensions either manually or by computer controlled positioning means, e.g., those used for positioning robotically controlled tools, if desired.

Tissue can be removed or affected by several processes, including vaporization; cross linkage, which produces shrinkage; disruption of cellular membranes; desiccation of fat cells; lipolysis or melting of fat cells; melting and fusion of tissue components (welding) and denaturation or coagulation of proteins. Little bleeding occurs during such processes due to the hemostasis produced by the effects of the applied light energy. The effects produced depend on the wavelength and energy level used. The process of tissue ablation requires relatively higher energy levels. Tissue welding may be used to join opposed tissue surfaces at relatively low energy levels, without the need for sutures and their subsequent removal.

Blood and tissue coagulation is produced by heating the tissue to at least about 62 degrees Celsius. Tissue vaporization or ablation is produced by heating the tissue to at least about 100 degrees Celsius, causing the water in the cells to turn into steam. The small volume of steam produced is rapidly cooled by interaction with the tissue, and quickly condenses. Tissue disruption may also be caused by attendant concurrent acoustic effects of laser energy emission.

The physiological response of the treated area progresses through a continuum of at least three phases of wound healing after superficial or percutaneous laser treatment. First, there is an edema phase, seen many cases within about 10 days after treatment. The sequence of events generally follows a course including two days of swelling and two days of subsidence. The second phase is characterized by the proliferation of fibroblasts. The third phase is the resolution phase in which tissue remodeling takes place.

The tissue in the region to be treated subcutaneously is preferably hydrated before laser treatment by the injection of water or an aqueous saline solution. The water or aqueous saline solution used for this purpose may include an acceptable local anesthetic. The overall treatment parameters of energy levels, pulse width and frequency typically used in illustrative procedures are tabulated in Table 1, below.

In each case, for penetration of the skin, the optical fiber is positioned perpendicular to the skin, and a very low level of light energy is emitted while very gentle pressure is applied. Typical parameters used for skin penetration are 3–10 mJ/pulse, preferably about 5 mJ/pulse, frequency of about 20–60 Hz and pulse width of about 40–80 $\mu$S, although skin penetration of the fiber optic can be achieved also through a trocar, hypodermic needle or an opening in the skin such as a needle puncture.

Similar energy parameters can be used to prevent or minimize tissue adherence while advancing the fiber to the treatment site or withdrawing the fiber from the treatment site. The preferred energy parameters for treatment at the site or along a tissue track, are set forth in Table 1.

TABLE 1

Preferred Parameters for Laser Treatment in Selected Procedures

| PROCEDURE | FREQUENCY Hz | ENERGY mJ/Pulse | PULSE WIDTH ($\mu$S) |
|---|---|---|---|
| Upper Blepharoplasty | 20–60 | 5–40 | 50–80 |
| Lower Blepharoplasty | 20–60 | 5–40 | 40–70 |
| Varicose Vein Coagulation | 20–60 | 5–40 | 70–90 |
| Varicose Vein Coagulation, Double pulse Mode* | 10–50 | 10–100 | 600–700 |
| Skin Wrinkle Removal | 20–60 | 5–40 | 40–70 |
| Telangiectasia | 20–60 | 5–40 | 40–100 |
| Permanent Hair Removal | 20–60 | 5–20 | 40–70 |

*Double pulse mode can be used to achieve long pulse width for greater coagulative effect (see EXAMPLE 8, below).

The laser tissue effect on the selected tissue site can be controlled by modulating the energy per pulse, repetition rate and/or pulse width of the emitted laser energy.

EXAMPLE 1

Subcutaneous Localized Treatment Parallel to the Skin Surface

The areas selected for treatment are first hydrated by an injection of water, an aqueous saline solution, or, preferably, an aqueous saline solution containing an appropriate local anesthetic. The injected liquid serves to absorb excess light energy and heat, to cool the tissue and to provide a buffer zone, which is especially useful in some locations, such as around the eyes.

The tip of the optical fiber is placed on the skin surface, at about a 90 degree angle to the skin surface. The optical fiber is a bare optical fiber of about 100 $\mu$m to about 365 $\mu$m in core diameter, preferably about 200 $\mu$m core diameter. The tip pierces the skin and is advanced into the subcutaneous tissue while emitting laser energy at about 5 mJ/pulse, a pulse width of about 40 to about 70 $\mu$S at a frequency of about 20 to about 60 Hz. Low energies are used to minimize adverse thermal effects, such as scarring, depigmentation or hyperpigmentation, at the site of entry.

After insertion of the tip of the optical fiber though the skin, the fiber is turned so that it is roughly parallel to the plane of the skin surface. The fiber is advanced and withdrawn repeatedly as needed to treat the selected region. Energy emission at 1.55 $\mu$m is increased after the initial advancement stage to a therapeutic level of about 5 to about 50 mJ/pulse, depending on the diameter of the fiber, smaller fibers requiring less energy. Preferably, about 20 mJ/pulse is used at about the same pulse width and frequency. The optical fiber is moved axially to and from, but not swept laterally like a windshield wiper. The treatment of a selected area is continued until audible cavitation sounds ("popping") cease. Such cavitation sounds signal the destruction of the fat present at the site (lipolysis) and the heating of the collagen. The optical fiber is then withdrawn from the skin, while continuing to emit energy at or below the therapeutic level, in order to minimize the amount of tissue adhering to the tip of the optical fiber.

This method is used when the primary objective is the removal of fat or the coagulation of blood vessels, with a secondary objective of tightening the skin. This method is appropriate, for example, for lipolysis of the fat pads and tightening (blepharoplasty) of the upper and lower eyelids, removal of nasal labial folds, removal of perioral and periorbital wrinkles; treatment of marionette lines and wrinkles of the ear lobes; neck lifts and lip lifts. This method can also be used for coagulation of telangiectasias, varicose and spider veins, hemiangiomas and rosacea.

EXAMPLE 2

Percutaneous Localized Treatment Non-Parallel to Skin Surface

The method of Example 1 is used with the modification that the optical fiber is directed to the treatment site or used along a treatment track that is not parallel to the plane of the skin surface. This method is appropriate, for example, for the treatment of polly beak, wherein the shape of the nose is lifted and reshaped as desired by producing tissue shrinkage combined with lipolysis. For this purpose, the frequency used is about 20 to about 60 Hz; all other parameters as the same as described in Example 1. This method is useful when the primary objective is the removal of fat or removal of excess vascularization, with a secondary objective of tissue shrinkage to tighten the skin.

EXAMPLE 3

Tattoo Removal

Tattoo removal is accomplished by inserting the tip of the optical fiber through the skin in the pigmented area, at the fiber penetration energy parameters as described above, keeping the optical fiber perpendicular to the skin or tilting it at an angle substantially parallel to the skin and advancing and withdrawing the optical fiber while emitting energy at the parameters as described in Example 1. Subsequent additional penetrations are made until the entire pigmented area is treated.

EXAMPLE 4

Incision (Internal Weir)

A bare optical fiber about 365 $\mu$m in diameter is inserted at the base of the nostril. The method of Example 1 is used to create a wedge-shaped trough or channel; the parameters are: about 10 mJ/pulse to about 50 mJ/pulse, pulse width 50–70 $\mu$S and frequency about 20 to about 60 Hz. The edges of the channel are sutured together to reduce the size of the nostril opening.

EXAMPLE 5

Cartilage Vaporization, Bone Reduction

This method is useful for rhinoplasty (commonly referred to as a nose job), which can be performed without postoperative bruising and black eyes. Series of holes are made through the skin and through cartilaginous and bony tissue using the optical fiber. The holes are placed at or around the nose ridge protrusion in a configuration like the perforations at the edges of a postage stamp. During the entry phase, the tip of the 200 or 365 $\mu$m bare optical fiber is placed at a 90 degree angle relative to the skin. The fiber enters the skin through a trocar or needle puncture, or low penetration energies (about 5 mJ/pulse), can be used to minimize thermal effect at the skin entrance point. Therapy is administered by advancing the fiber internally through cartilaginous and/or bony tissue. Energy parameters for therapy are 15–40 mJ/pulse, 40–70 $\mu$S pulse width, at 20–60 Hz. After the "postage stamp" configuration is completed, external pressure is applied to the "postage stamp" to dislocate it from its original structural connections. The cartilaginous/bone fragment may be left in the body to be naturally absorbed over time.

EXAMPLE 6

Tissue Transplantation

This method is useful for removal of patches of skin bearing hairs for transplantation into bald areas where hairless skin has been removed, as well as for transplantation of patches of normal skin onto burned surfaces. In both cases, the laser enables the patches to be removed without bleeding. The patches can be affixed by welding their edges to the existing tissue, with less bleeding and scabbing, and with faster healing.

The tissue is hydrated by the injection of water, saline or preferably, an aqueous solution of local anesthetic, as described in Example 1. The bare patch of skin is excised using a 200–365 $\mu$m bare optical fiber emitting energy at 20–40 mJ/pulse, 40–70 $\mu$S pulse width, at 20–60 Hz. The patch of skin bearing hair is implanted in place, and the edges sealed to the adjacent skin using the parameters of 10–25 mJ/pulse, 30–70 $\mu$S pulse width, 20–60 Hz.

EXAMPLE 7

Coagulation of Varicose Veins

This method is useful for treatment of varicose veins. The area surrounding the veins to be treated is anesthetized. The optical fiber, preferably a bare optical fiber, about 200 $\mu$m to about 365 $\mu$m in diameter, is placed on the skin above one end of the visible portion of the vein to be treated. The optical fiber penetrates the surface of skin at about a 90 degree angle and enters the vein, using parameters of about 5 mJ/pulse, 50–90 $\mu$S pulse width and 20–60 Hz. The energy is increased to about 5–25 mJ/pulse, preferably about 15 mJ/pulse, with the optical fiber tip within the vein. Treatment is continued until the vein is coagulated. After the treatment, the tip of the optical fiber is withdrawn while lasing at the therapeutic parameters, i.e. about 5–25 mJ/pulse, preferably about 15 mJ/pulse, 70–90 $\mu$S pulse width and 20–60 Hz. The treatment is repeated at the other end of the visible portion of the varicose vein.

Alternatively, a laser generating energy in a double pulse mode is used in the treatment of varicose veins. In the double pulse mode, a periodic burst of pulses comprising two or more pulses close together in time is produced (instead of a train of equally spaced pulses), thereby increasing the effective duration of the pulse length and thus the coagulative effect. The treatment protocol as described above is modified by the use of pulses about 600$\mu$S to about 700 $\mu$S in width at about 10 Hz to about 30 Hz. The energy levels used are the same as described above, i.e. about 5 mJ/pulse during penetration and about 15 mJ/pulse during therapy. In relatively larger veins, up to 50 mJ per pulse is emitted to coagulate a relatively larger volume of blood.

EXAMPLE 8

Permanent Hair Removal

Hair removal is accomplished by inserting a small diameter optical fiber directly into the hair follicle, and applying an appropriate amount of laser energy, i.e., sufficient to coagulate or vaporize the hair follicle. This treatment disables the follicle and prevents regrowth of the hair. The diameter of the tip of the optical fiber is in the range of about 25 $\mu$m to about 100 $\mu$m. Preferably the diameter of the tip of the optical fiber is about 50 $\mu$m. While the fiber may be manually inserted into the hair follicle, with the user employing a loupe or a magnifying device, for the treatment of large areas, a computer-controlled three dimension, x, y, z axis positioning device, as is used in industry for robotically applied tools, along with an optical scanner programmed to recognize hair follicles may be used. Laser energy parameters that are useful are: 5–25 mJ/pulse, 30–70 $\mu$S pulse width, 20–60 Hz.

The foregoing is intended to be illustrative of the present invention, but not limiting. Numerous variations and modifications may be effected without departing from the true spirit and scope of the invention.

We claim:

1. A method for percutaneous laser treatment of a patient having a condition requiring treatment, comprising the steps of:

selecting the area to be treated;
   selecting an appropriate source of light energy having a wavelength of less than 2 micrometers;
   selecting an optical fiber of appropriate core diameter;
   inserting the tip of the optical fiber through an opening in the patient's skin into tissue;
   advancing the tip of the optical fiber through tissue;
   treating the tissue;
   withdrawing the tip of the optical fiber through the tissue; and
   emitting the light energy through the tip of the optical fiber at an energy level less than about 200 milliJoules per pulse, with a pulse width less than about 200 microseconds and at an energy emission frequency of about 20 to 80 Hertz while treating the tissue when advancing or withdrawing the tip of the optical fiber.

2. A method for percutaneous laser treatment of a patient having a condition requiring treatment, comprising the steps of:

selecting the area to be treated;
   selecting an appropriate source of laser energy having a wavelength of less than 2 micrometers;
   selecting an optical fiber of appropriate core diameter;
   inserting the tip of the optical fiber through an opening in the patient's skin into tissue;
   advancing the tip of the optical fiber through tissue;
   treating the tissue;
   withdrawing the tip of the optical fiber through the tissue;
   emitting the laser energy through the tip of the optical fiber at a energy level less than about 200 milliJoules per pulse, with a pulse width less than about 200 microseconds and at an energy emission frequency of greater than about 5 Hertz while treating the tissue; and
   emitting pulsed laser energy through the tip of the optical fiber at a selected energy level less than about 100 milliJoules per pulse, with a pulse width less than about 100 microseconds and at an energy emission frequency greater than about 20 Hertz while the tip of the optical fiber is advanced through the tissue.

3. A method for percutaneous laser treatment of a patient having a condition requiring treatment, comprising the steps of:

selecting the area to be treated;
   selecting an appropriate source of light energy having a wavelength of less than 2 micrometers;
   selecting an optical fiber of appropriate core diameter;
   inserting the tip of the optical fiber through an opening in the patient's skin into tissue;
   advancing the tip of the optical fiber through tissue;
   treating the tissue;
   withdrawing the tip of the optical fiber through the tissue;
   emitting light energy from the tip of the optical fiber while the tip of the optical fiber is inserted through the skin at an energy level of about 3 milliJoules per pulse to about 20 milliJoules per pulse; and
   emitting the light energy through the tip of the optical fiber at a energy level less than about 200 milliJoules per pulse, with a pulse width less than about 200 microseconds and at an energy emission frequency of greater than about 5 Hertz while treating the tissue.

4. A method for percutaneous laser treatment of a patient having a condition requiring treatment, comprising the steps of:

selecting the area to be treated;
   selecting an appropriate source of laser energy having a wavelength of less than 2 micrometers;
   selecting an optical fiber of appropriate core diameter;
   inserting the tip of the optical fiber through an opening in the patient's skin into tissue;
   advancing the tip of the optical fiber through tissue;
   treating the tissue;
   withdrawing the tip of the optical fiber through the tissue; and
   emitting pulsed laser energy through the tip of the optical fiber at an energy emission level of about 3 milliJoules per pulse to about 20 milliJoules per pulse, with a pulse width less than about 200 microseconds and an energy emission frequency greater than about 5 Hertz while advancing the tip of the optical fiber.

5. The method of claim 3 wherein the energy emission frequency while the tip of the optical fiber is inserted through the skin is about 20 to 80 Hertz.

6. The method of claim 1 wherein the energy emission level while the tip of the optical fiber is advanced or withdrawn through tissue is about 5 milliJoules per pulse to about 50 milliJoules per pulse.

7. The method of claim 1 wherein the pulse width is 5 to 100 microseconds.

8. The method of claim 1 wherein the light energy is obtained from a Nd:YAG laser.

9. The method of claim 1 wherein the light energy is obtained from a excimer laser.

10. The method of claim 1 wherein the light energy is obtained from an argon laser.

11. The method of claim 1 wherein the light energy is obtained from a KTP laser.

12. The method of claim 1 wherein the light energy is obtained from a diode laser.

13. The method of claim 1 wherein the light energy is obtained from a 1.064 μm Nd:YAG laser.

14. The method of claim 1 wherein the light energy is obtained from a erbium laser.

15. The method of claim 1 wherein the light energy is obtained from a high intensity white light generator.

16. The method of claim 1 wherein the tissue is skin tissue.

17. The method of claim 1 wherein the tissue is tissue underlying the skin.

18. The method of claim 1 wherein the condition requiring treatment is blepharochalasis.

19. The method of claim 1 wherein the condition requiring treatment is dermochalasis.

20. The method of claim 1 wherein the condition requiring treatment is turkey neck.

21. The method of claim 1 wherein the condition requiring treatment is rosacea.

22. The method of claim 1 wherein the condition requiring treatment is plantar warts.

23. The method of claim 1 wherein the condition requiring treatment is keloid scars.

24. The method of claim 1 wherein the condition requiring treatment is telangiectasia.

25. The method of claim 1 wherein the condition requiring treatment is wrinkles.

26. The method of claim 1 wherein the condition to be treated is unwanted hair follicles.

27. The method of claim 1 wherein the condition to be treated is the pigmented area of a tattoo.

28. The method of claim 1 wherein the condition requiring treatment is marionette lines.

29. The method of claim 1 wherein the condition requiring treatment is basal cell carcinoma.

30. The method of claim 1 wherein the condition requiring treatment is acne scars.

31. The method of claim 1 wherein the condition requiring treatment is chicken pox scars.

32. The method of claim 1 wherein the condition requiring treatment is age spots.

33. The method of claim 1 wherein the condition requiring treatment is hemangioma.

34. The method of claim 1 wherein the condition requiring treatment is port wine stains.

35. The method of claim 1 wherein the condition requiring treatment is hyperpigmentation.

36. The method of claim 1 wherein the condition requiring treatment is varicose veins.

37. The method of claim 1 wherein the condition requiring treatment is polly beak.

38. A method for percutaneous laser treatment of a patient requiring treatment, comprising the steps of:

selecting the area to be treated;

selecting an appropriate source of laser energy having a wavelength of less than 2 micrometers;

selecting an optical fiber of appropriate core diameter;

inserting the tip of the optical fiber through an opening in the patient's skin into tissue;

advancing the tip of the optical fiber through tissue;

treating the tissue;

withdrawing the tip of the optical fiber through the tissue; and emitting the laser energy through the tip of the optical fiber in a double pulse mode to produce and effect pulse width of up to about 700 μS, at a energy level less than about 200 milliJoules per pulse, and at an energy emission frequency of greater than about 5 Hertz while treating the tissue, wherein the condition requiring treatment is varicose veins.

* * * * *